(12) United States Patent
Corbett

(10) Patent No.: US 7,182,509 B2
(45) Date of Patent: Feb. 27, 2007

(54) NANOLITER OSMOMETER AND METHOD OF OPERATION

(75) Inventor: Christopher J. Corbett, Norwell, MA (US)

(73) Assignee: Advanced Instruments, Inc., Norwood, MA (US)

( * ) Notice: Subject to any disclaimer, the term of this patent is extended or adjusted under 35 U.S.C. 154(b) by 114 days.

(21) Appl. No.: 11/115,115

(22) Filed: Apr. 27, 2005

(65) Prior Publication Data

US 2006/0245466 A1    Nov. 2, 2006

(51) Int. Cl.
*A61B 5/01* (2006.01)
*G01N 33/48* (2006.01)
*G01N 13/04* (2006.01)
*G01N 25/04* (2006.01)

(52) U.S. Cl. .................. 374/16; 600/549; 600/573; 600/318; 422/68.1; 702/139; 73/64.47

(58) Field of Classification Search ................. 374/16, 374/18–20; 422/68.1; 702/139; 703/64.47; 600/549, 573, 318
See application file for complete search history.

(56) References Cited

U.S. PATENT DOCUMENTS

| | | | |
|---|---|---|---|
| 3,164,982 A * | 1/1965 | Pasternak et al. .......... | 73/64.47 |
| 3,203,226 A | 8/1965 | Fiske, Jr. | |
| 3,498,113 A * | 3/1970 | Whatley .................... | 73/61.76 |
| 4,269,197 A | 5/1981 | Gilbard | |
| 4,400,096 A * | 8/1983 | Molloy ........................ | 374/25 |
| 4,601,587 A * | 7/1986 | Mathiprakasam ........... | 374/25 |
| 4,657,409 A | 4/1987 | Wiggin et al. | |
| 4,907,896 A * | 3/1990 | Martuscello et al. ........ | 374/190 |
| 4,951,683 A | 8/1990 | Davis | |

(Continued)

FOREIGN PATENT DOCUMENTS

JP    357 161531    1/1982

*Primary Examiner*—Gail Verbitsky
(74) *Attorney, Agent, or Firm*—Antonelli, Terry, Stout and Kraus, LLP.

(57) ABSTRACT

The invention is an apparatus for determining a temperature at which a phase change occurs in a fluid sample, a method for measuring a temperature at which a phase change occurs in a sample and a sample cell. An apparatus for determining a temperature at which a phase change occurs in a fluid sample 60' in accordance with the invention includes a sample cell (12')for providing direct collection of the sample from a sample source (74) which is collected and retained at a collecting end thereof by capillary attraction between the collecting end and the sample, the sample cell including a longitudinal passage (78) extending from the collecting end to a far end through which light is transmitted to provide an image of the sample as retained at the collecting end of the passage and with a cross sectional area of the passage being greater at the far end than at the collecting end; a heating and cooling assembly (14), including a temperature sensing device (44), the heating and cooling assembly holding and thermally contacting the sample cell during the determining of the temperature by the temperature measuring device at which the phase change occurs while the sample is positioned in the collecting end; and an illumination system (16) for directing a light beam to the collecting end, through the sample, through the longitudinal passage and out of the far end to permit viewing of the sample from the far end to determine the temperature at which the phase change occurs.

42 Claims, 7 Drawing Sheets

U.S. PATENT DOCUMENTS

| | | |
|---|---|---|
| 4,996,993 A | 3/1991 | York |
| 5,088,833 A | 2/1992 | Tsang et al. |
| 5,143,080 A | 9/1992 | York |
| 5,192,665 A | 3/1993 | Salonen |
| 5,230,864 A * | 7/1993 | Columbus .................... 422/100 |
| 5,279,793 A * | 1/1994 | Glass ....................... 422/82.06 |
| 5,758,968 A | 6/1998 | Diebold |
| 6,438,398 B1 | 8/2002 | Pflugfelder et al. |
| 2003/0225341 A1 * | 12/2003 | Ruether et al. .............. 600/549 |
| 2005/0159657 A1 * | 7/2005 | Cappo et al. ................ 600/315 |
| 2006/0137435 A1 * | 6/2006 | Sullivan ..................... 73/64.47 |

* cited by examiner

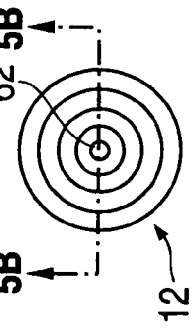
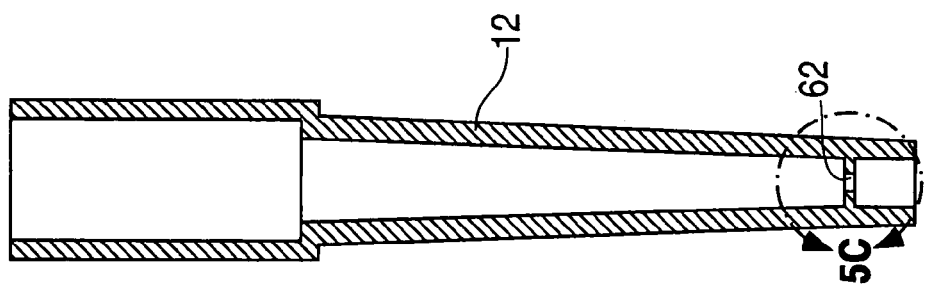
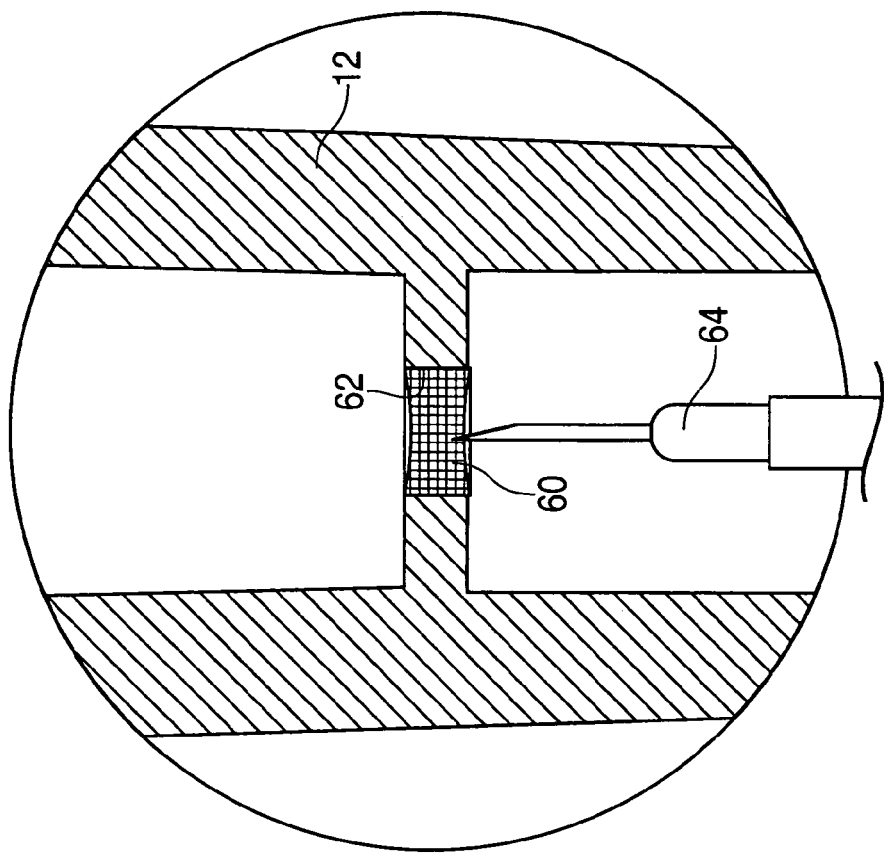

NANOLITER OSMOMETER AND METHOD OF OPERATION

BACKGROUND OF THE INVENTION

The present invention relates to the determination of the temperature at which a phase change occurs in a fluid sample such as, but not limited to, osmometers and the method of use thereof.

DESCRIPTION OF THE PRIOR ART

Recently, interest has developed in using osmometry on extremely small samples of fluid, such as, a sample of a human eye tear. Handling of nanoliter samples is complicated by the physical size of the sample. One prior art technique utilizes a plate containing depressions which hold portions of the sample. This technique recognizes the last portion of the sample to melt with reflective light technology.

The Assignee has developed an osmometer as described below with respect to FIGS. 1–5A–5C. The osmometer described below of the Assignee, while functioning to determine the point of phase change from a frozen tear sample to liquid did, not have the desired ease of use.

FIG. 1 illustrates a system diagram of the prior art nanoliter osmometer system 10 of the Assignee. The osmometer 10 includes a sample cell 12 which holds a sample as illustrated in FIG. 5C. The sample cell 12 is positioned within a heating and cooling assembly 14. Illumination of the sample is provided by the LED light source 16. Illumination from the LED 16 passes into the sample contained within the sample cell 12 positioned at the end proximate to the LED 16, through the longitudinal passage therein and out the far end in proximity to a video microscope 18 and to a CCD camera 20 located at the focal plane of the microscope. The video output from the CCD camera 20 is displayed by display 22 to permit an operator viewing of the sample when it changes phase from a frozen state to a liquid state. The video output from the camera CCD camera 20 is fed to a computer 24 that provides recording and image analysis functions which also detects through the use of software a phase transition point at which the last portion of the sample melts, which is used to determine the precise temperature of the melting point which in turn is used to determine the osmolality of the sample. Temperature control of the heating and cooling assembly 14 is accomplished by a temperature controller 36 that is discussed in more detail below with respect to FIG. 2.

FIG. 2 is an exploded view illustrating in more detail the heating and cooling assembly 14 of FIG. 1. In proximity to the LED 16, fluid inlet and outlet nipples 28 supply heating or cooling fluid from a fluid source (not shown) to a heating or cooling block 30. The heating and cooling block 30 is sealed to a thermal stage 32 by O-rings 34. A LED holder holds the LED 16 in a position to illuminate the sample 60 contained with the sample cell 12 as described below. A thermoelectric cooling device 38 is controlled by the temperature controller 26 by means of electrical leads 40. The sample cell tip cooling block 42 is in thermal contact with the sample cell 12 during use and contains a temperature sensor 44 that provides a temperature read out to the temperature controller 26 of FIGS. 1 and 2 by leads 52. The thermal sensor 44, which may be a thermistor, is located within the cooling tip block 42. A thermal spacer 46 is positioned between the cooling block 42 and the top cooling plate 48. The thermal sensor 44 is connected to standoffs 50 which are connected to the temperature controller 26 by leads 52. Fasteners for holding together the exploded assembly of FIG. 2 have been omitted.

FIGS. 3 and 4 respectively illustrate an isometric view of the assembled heating and cooling assembly 14 with the sample cell surrounded by insulating foam 56 and a cross-sectional view of the heating and cooling assembly without the insulating foam. As may be seen in FIG. 3, the insulating foam 56 surrounds the sample holder 12 to provide thermal isolation from the environment and thermal contact with heating and cooling assembly 14 which provides even heating or cooling of the sample located within the sample cell 12 and aligns the sample cell with the thermoelectric cooling device 38 and the light produced by the LED 16 for illuminating the sample 60 therein to be viewed by the CCD camera 20. As may be seen from FIG. 1, the CCD video camera 20 is vertically adjustable so that the object plane of the camera and the depth of field of the microscope 18 is sufficient to encompass the thickness of the sample 60.

FIGS. 5A–5C illustrate the sample holder 12 of the Assignee's prior art design. The sample 60 is held by capillary attraction and surface tension within the circular bore 62 in the sample cell. The diameter of the bore (annular ring) 62 in the Assignee's prior osmometer was 0.034 inches and had a maximum sample thickness of 0.017 inches. As is apparent from FIGS. 5B and 5C, the sample 60 is held within the bore 62 at the tip of the sample cell 12. The sample 60 is placed in the bore by a syringe 64.

A glass capillary tube was placed in the patient's eye to fill the tube with a volume of approximately 200 nanoliters. The operator then transferred the sample from the glass capillary tube to a syringe 64 or other suitable device. The syringe 64 or other suitable device was used to place the sample 60 within the recessed bore 62 as illustrated in FIGS. 5B and 5C. The sample cell 12 has a rigid hollow tapered body with an approximate length of 1.5 inches containing an appropriately sized hole to retain the sample. The sample 62 was deposited into the center of the annular ring in the bore 62 at the tip of the cell by the syringe 64. The sample 60 was held in place in the bore 62 by surface tension and capillary attraction at the perimeter of the bore. The operator then manually inserted the sample cell 12 into the cooling block 42 as illustrated in FIG. 4 so that the outside surface thereof makes intimate physical contact with the internal profile of the sample cooling block.

When a test is initiated with the Assignee's model 3000 osmometer, the temperature controller 36 and computer 24 control the amount of heat that is extracted from the sample cooling block 42 by the thermoelectric cooling device 38. The thermoelectric cooling device 38 within the cooling block 42 and the sample cell 12 are held in close physical and thermal contact with one another to insure effective thermal control of the sample site. The temperature controller 26 supercools the sample well below its freezing point to approximate value of −30° C. At this point, the sample spontaneously freezes. This is observed visually through an optical imaging system including the CCD camera 20 and microscope 18 positioned on one side of the sample with the illumination source which is the light emitting diode 16 positioned on the other side. The illumination from the LED 16 projects light through the sample, creating a series of images that are acquired by the CCD camera 20. These images are processed by the image analysis software and are also displayed on the computer monitor 22 or other suitable display. Prior to freezing, the sample appears translucent as light from the illuminating LED 16 passes through the sample 60 via the sample cell 12. Upon freezing, the sample appears opaque because the freezing process occludes light from the LED 16 passing through the sample 60.

Once the software within the computer 24 and the temperature controller 26 determines that the sample 60 has frozen using known image processing logic, the temperature controller 36 reduces the amount of heat extracted from the cooling block 42 allowing the sample temperature to arise at predicted rates. Prior to establishing the last rate of heat extracted from the sample 60, the sample temperature is held constant for a set time period to establish thermal equilibrium in the system. Once a thermal equilibrium is established, the temperature controller 36 allows the temperature to rise and melt the sample 60.

Just prior to the melting point of the sample 60, the image of the sample becomes less opaque and distinct solid crystals can be visually detected by analysis of the CCD images and/or the software resident in the computer 24. The melting point of the sample 60 is determined visually by the optics and software as the point when the last solid crystal melts. This is determined by applying several known criteria that monitor the change in the overall light intensity transmitted through the sample 60. At the point that the melting point is established, the system notes the temperature from the thermal sensor 44 located in the cooling block 42 adjacent to the sample 60 and mathematically converts it to a corresponding value of osmolality using techniques which are well known in the art which need not be described for the practice of the invention. The result is displayed on the display 22 or other applicable display. The thermal sensor 44 has been previously calibrated using a series of prepared saline solutions with known melting points and a computerized calibration routine.

Several limitations exist with the aforementioned design of the sample cell 12 used with the model 3000 osmometer of the Assignee. The extremely small size of the sample (approximately 200 nanoliters) necessitates a high level of manual dexterity to transfer the sample from the collection capillary (not illustrated) into the syringe 64 and into the sample cell 12 to be inserted into thermal contact with the heating and cooling assembly 14. In conjunction with the physical transfer from the syringe 60 into the sample cell 12, the operator must insure that the sample is uniformly deposited and confined within the bore 62 of a sample cell 12, so that it can be properly viewed by the optical system which, in practice, has been a source of non-uniform determinations of the temperature at which a phase change occurs and determination of osmolality.

SUMMARY OF THE INVENTION

The present invention is an apparatus for determining a temperature at which a phase change occurs in a fluid sample, a method for measuring a temperature at which a change phase occurs in a sample and a sample cell. The present invention overcomes the problems of the prior art as described above and provides a sample cell which may be used directly for collection of the sample in conjunction with the prior art instrument described above for measuring osmolality of a sample. The direct collection may be by utilizing the sample cell to obtain a required volume of a sample by placing the tip of the sample cell in the corner of a patient's eye. The exterior shape and internal dimensions of the sample cell and the material used for the construction of the sample cell are designed to provide direct acquisition and retention of the sample at the tip of the sample cell based upon affinity of the sample for the type of material used to manufacture the sample cell thus enhancing the measuring of the temperature at which the phase of the sample changes and further obtaining sample osmolality. A preferred application of the present invention is the utilization of the sample cell to directly collect and measure the osmolality of human body fluids such as tears.

The sample cell in accordance with the invention provides direct collection of a sample from a sample source which is collected and retained at a collecting end thereof by capillary attraction between the collecting end and the sample. The sample cell includes a longitudinal passage extending from the collecting end to a far end through which light is transmitted to provide an image of the sample as retained at the collecting end of the passage with the cross-sectional area of the passage being greater at the far end than at the collecting end. The longitudinal passage at the collecting end comprises a section which collects and retains a sample by the capillary attraction which extends from an opening at the collecting end into the passage. A tapered section tapers outwardly in the interior of the longitudinal passage at the collecting end thereof toward the far end to provide a greater area at the far end of the passage whereby the collecting end contains the sample to achieve a repeatable minimum collected sample volume in the collecting end to improve the consistency in determining the temperature at which the phase change occurs.

An apparatus for determining a temperature at which a phase change occurs in a fluid sample in accordance with the invention includes a sample cell for providing direct collection of the sample from a sample source which is collected and retained at a collecting end thereof by capillary attraction between the collecting end and the sample, the sample cell including a longitudinal passage extending from the collecting end to a far end through which light is transmitted to provide an image of the sample as retained at the collecting end of the passage and with a cross sectional area of the passage being greater at the far end than at the collecting end; a heating and cooling assembly, including a temperature sensing device, the heating and cooling assembly holding and thermally contacting the sample cell during determining of the temperature by the temperature measuring device at which the phase change occurs while the sample is positioned in the collecting end; and an illumination system for directing a light beam to the collecting end, through the sample, through the longitudinal passage and out of the far end to permit viewing of the sample from the far end to determine the temperature at which the phase change occurs. A temperature measuring device may be associated with the heating and cooling assembly which determines the temperature of the sample held in the sample cell when the sample cell is in thermal contact with the heating and cooling assembly. The longitudinal passage at the collecting end may comprise a section which collects and retains the sample by the capillary attraction which extends from an opening at the collecting end into the passage and a tapered section tapering outwardly from an interior end of the section within the passage toward the far end to provide the greater area at the far end of the passage whereby the collecting end contains the sample to achieve a repeatable minimum collected sample volume in the collecting end to improve consistency in determining the temperature at which the phase change occurs. The taper may be continuous. The sample cell may have at least one opening in proximity to the far end for equalizing air pressure in the passage during positioning of the sample cell in thermal contact with the heating and cooling assembly after collection of the sample. A camera may provide an image of the sample and a display device for reproducing the image provided by the camera. The illumination system may comprise a light emitting diode. The apparatus may be an osmometer for determining a concentration of solutes in a liquid solution of the sample. The sample may be human tears and the sample cell may have an exterior which tapers toward the near end to facilitate collection from an eye of a human. A wall of the sample cell may be substantially a same thickness along at least a longitudinal portion of the passage which is in thermal contact with the heating and the cooling assembly and a cylindrical section at the collecting end may have a diameter that is approximately twice that of the thickness. The sample cell may be manufactured from a plastic material providing at least partial reflection of the light beam from a surface of the longitudinal passage to enhance visual contrast between solid and liquid portions in the sample during a phase change of the sample.

A method for measuring a temperature at which a phase change occurs in a sample, with an apparatus including a temperature sensing device for sensing a temperature of the sample held in a sample cell to provide direct collection of the sample from a sample source which is collected and retained at a collecting end thereof by capillary attraction between the collecting end and the sample, the sample cell including a longitudinal passage extending from the collecting end to a far end through which light is transmitted to provide an image of the sample retained at the collecting end of the passage with a cross sectional area of the passage being greater at the far end than at the collecting end, a heating and cooling assembly including the temperature sensing device which holds and thermally contacts the sample cell during determining the temperature at which the phase change occurs by the temperature sensing device while the sample is retained at the collecting end, an illumination system for directing a light beam to the collecting end, through the sample, through the longitudinal passage and out of the far end to permit viewing of the sample to determine the temperature at which the phase change occurs in accordance with the invention includes positioning the collecting end of the sample cell in contact with a source of the sample to collect the sample by capillary attraction; positioning the sample cell in thermal contact with the heating and cooling assembly; cooling the sample within the sample cell to cause a first phase change in the sample by refrigerating the sample with the heating and cooling assembly; raising the temperature with the sample within the sample cell with a controlled temperature gradient provided by the heating and cooling assembly to cause a second phase change in the sample; illuminating the collecting end of the sample cell with light from the illumination system during the cooling and heating of the sample to direct light through the collecting end, through the sample, along the longitudinal passage and out of the far end to provide an image of the sample; viewing the image of the sample from the far end to visually detect when a first phase change occurs upon freezing and a second phase change occurs upon melting the sample being completed by the application of the controlled temperature gradient; and determining the temperature sensed by the temperature sensing device when the second phase change caused by raising the temperature of the sample has occurred. The longitudinal passage may comprise a section which collects and retains the sample by the capillary attraction which extends from an opening at the collecting end into the passage and a tapered section tapering outwardly from an interior end of the section within the passage toward the far end to provide a greater area at the far end of the passage whereby at least the section at the collecting end contains the sample to achieve a repeatable minimum collected sample volume in the collecting end to improve a consistency in determining the temperature at which the phase change occurs. A wall of the sample cell may be substantially a same thickness along a portion of the passage which is in thermal contact with the heating and cooling assembly. The taper may be continuous. The sample cell may be at least one opening in proximity to the far end for equalizing air pressure in the passage during positioning of the sample cell in thermal contact with the heating and cooling assembly after directly collecting of the sample. A camera may provide an image of the sample and a display device for reproducing the image provided by the camera; and wherein the illumination system may provide illumination of the sample held in thermal contact with the heating and cooling assembly, the camera provides an image of the sample held in thermal contact with heating and cooling assembly and the display device reproduces the image of the sample. The determined temperature may be converted into an osmolarity of the sample.

A sample cell for use in an apparatus for determining a temperature at which a phase change occurs in a fluid sample including a heating and cooling assembly including a temperature sensing device, the heating and cooling assembly holding and thermally contacting the sample cell during the determining of the temperature by the temperature measuring device at which the phase change occurs while the sample is positioned in the collecting end, and an illumination system for directing a light beam to the collecting end, through the sample, through the longitudinal passage and out of the far end to permit viewing of the sample from the far end to determine the temperature at which the phase change occurs, wherein the sample cell has a tip which provides direct collection of the sample from a sample source which is collected and retained at a collecting end thereof by capillary attraction between the collecting end and the sample in accordance with the invention includes the sample cell including a longitudinal passage extending from the collecting end to a far end through which light is transmitted to provide an image of the sample as retained at the collecting end of the passage and with a cross sectional area of the passage being greater at the far end than at the collecting end.

BRIEF DESCRIPTION OF THE DRAWINGS

FIGS. 5A–5C illustrate the sample cell of the Assignee's prior art nanoliter osmometer.

Like parts are identified by like reference numerals throughout the drawings.

DESCRIPTION OF THE PREFERRED EMBODIMENT

The present invention provides an improved osmometer, method of operation and sample cell which may be practiced using Assignee's prior osmometer as described in FIGS. 1–4, but is not limited thereto. The sample cell, as illustrated in FIGS. 6A–6E, may be utilized in a modified version of the prior art of FIGS. 1–4 to achieve the benefits of the invention.

Figure 1:
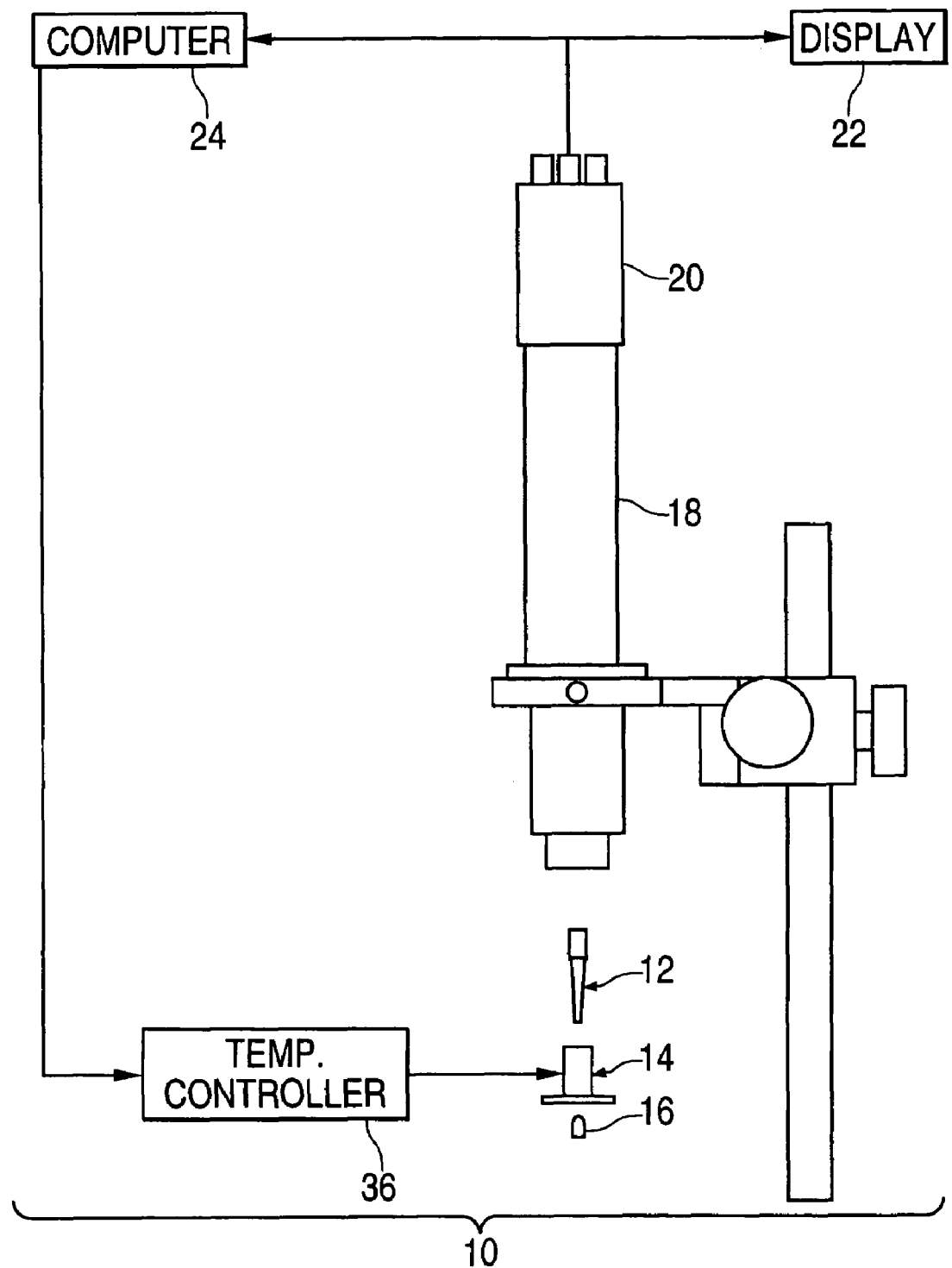
FIG. 1 illustrates a system diagram of the Assignee's prior art nanoliter osmometer.
Figure 2:
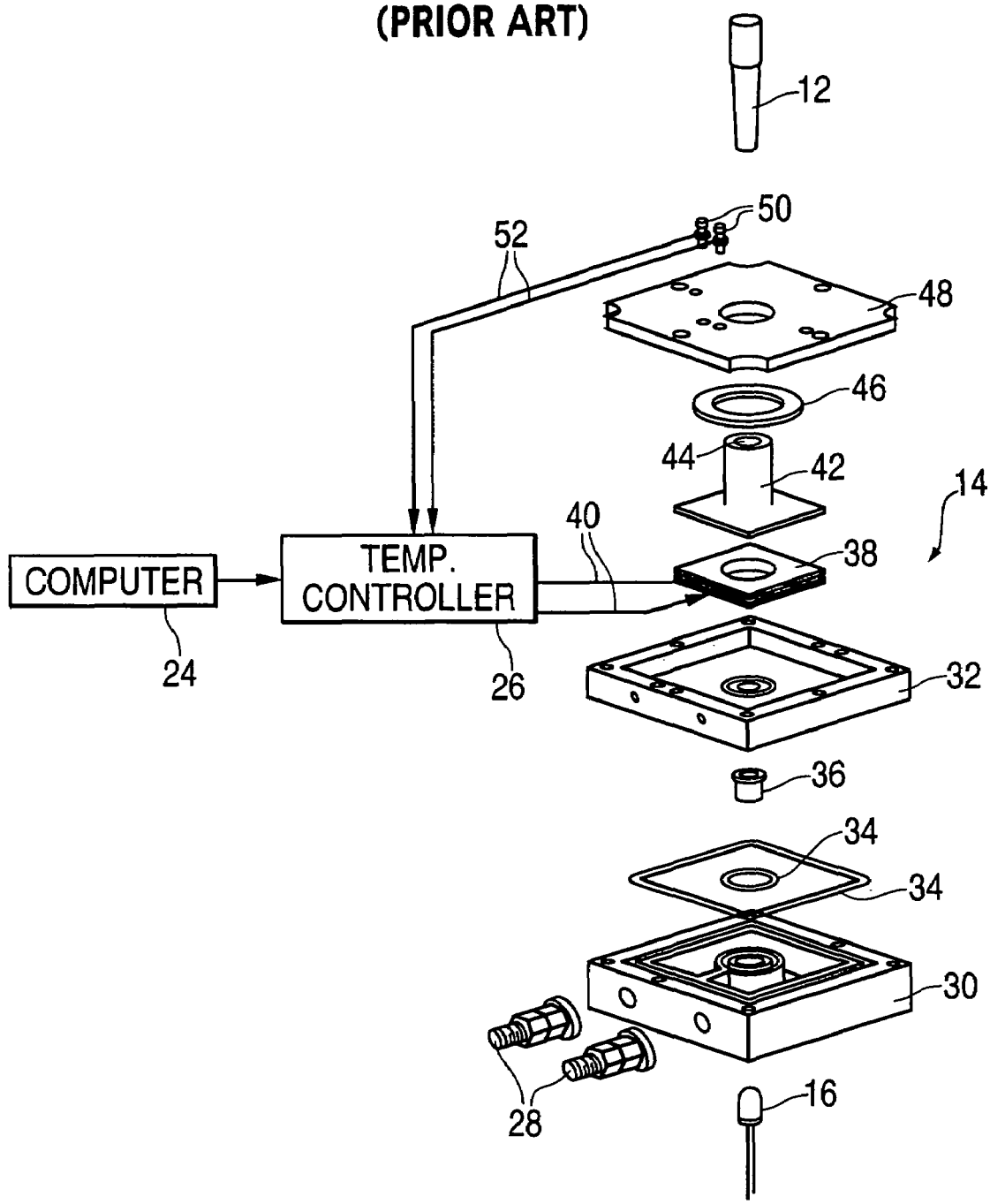
FIG. 2 is an exploded view of the heating and cooling assembly of the Assignee's prior art nanoliter osmometer.
Figure 3:
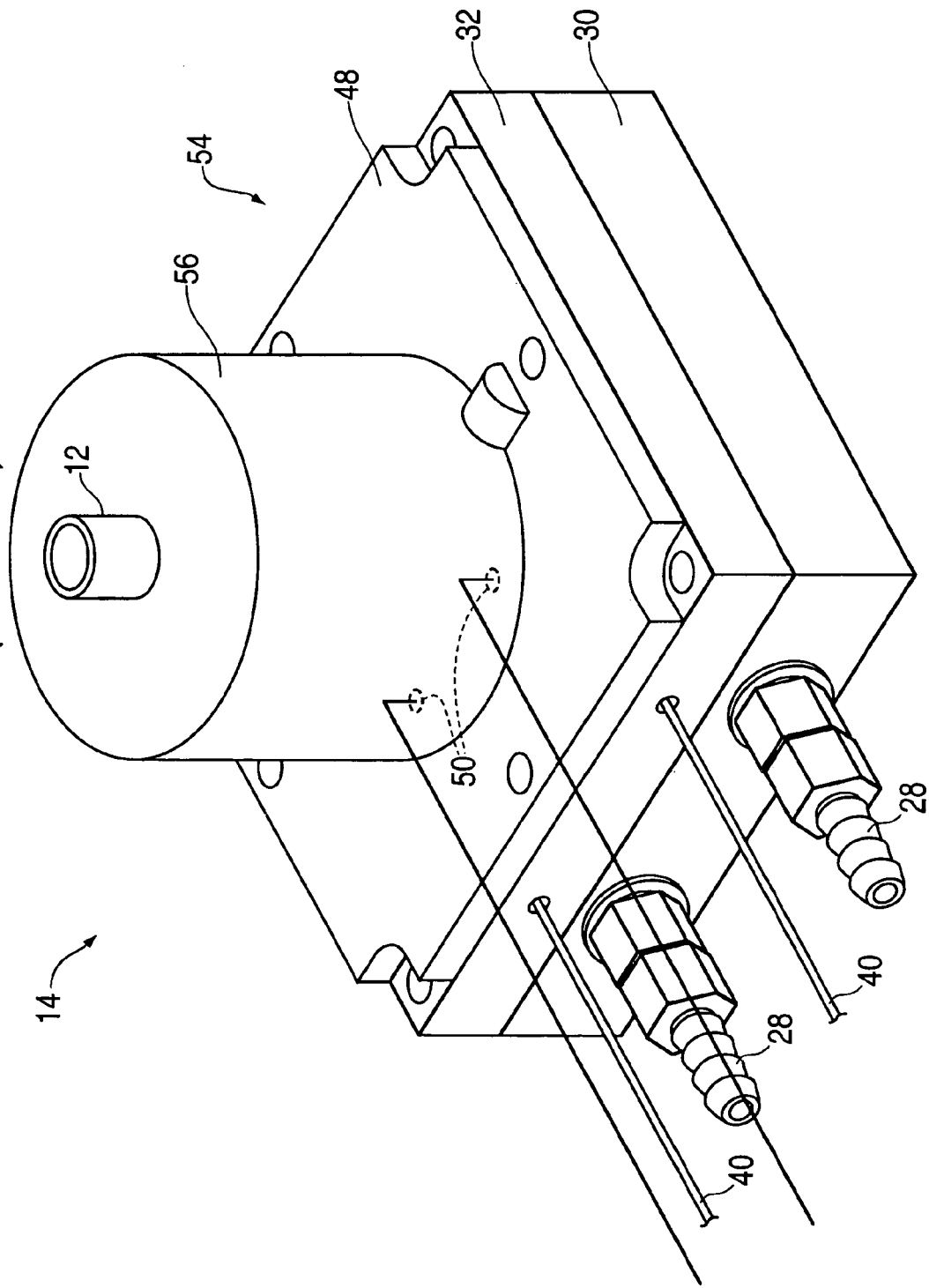
FIG. 3 is an isometric view of the heating and cooling assembly of the Assignee's prior art nanoliter osmometer with the sample cell being surrounded by insulating foam.
Figure 4:
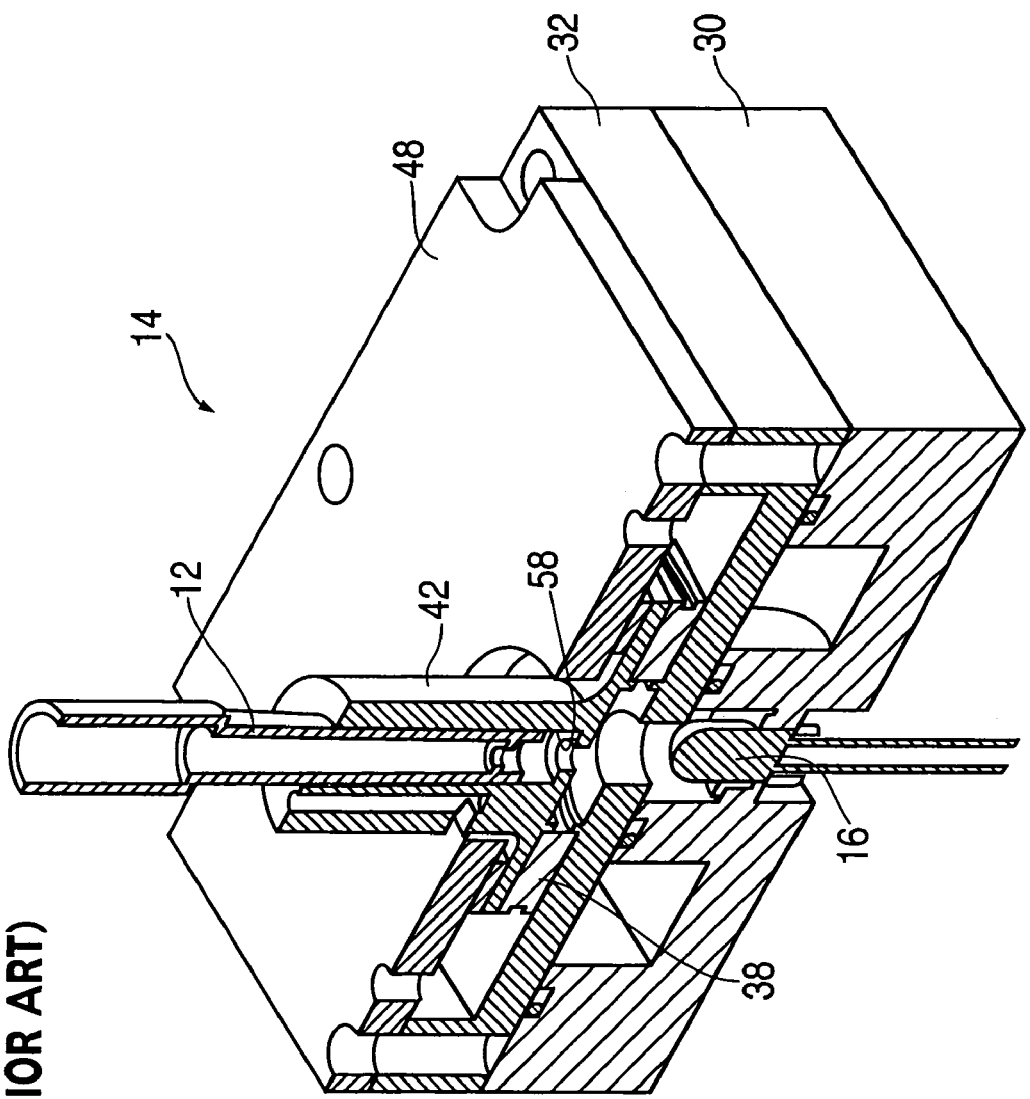
FIG. 4 is a sectional view corresponding to FIG. 3.
Figure 6A:
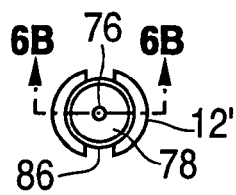
FIGS. 6A–6E illustrate a construction of an embodiment of the sample cell of the present invention including the direct collection of a sample of human tears.
Figure 6B:
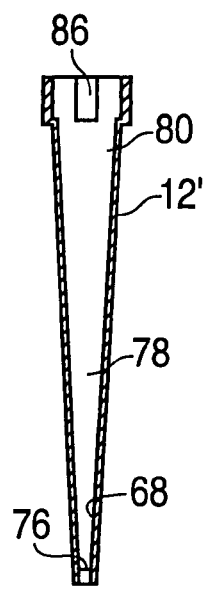
Figure 6C:
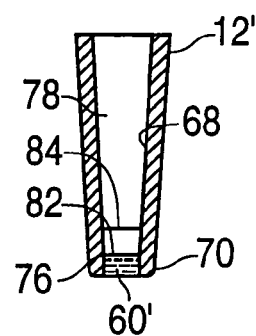
Figure 6D:
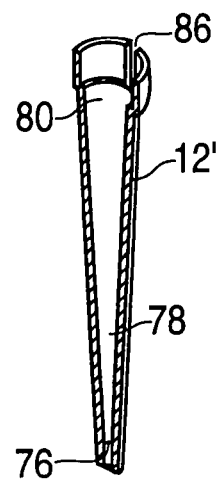
Figure 6E:
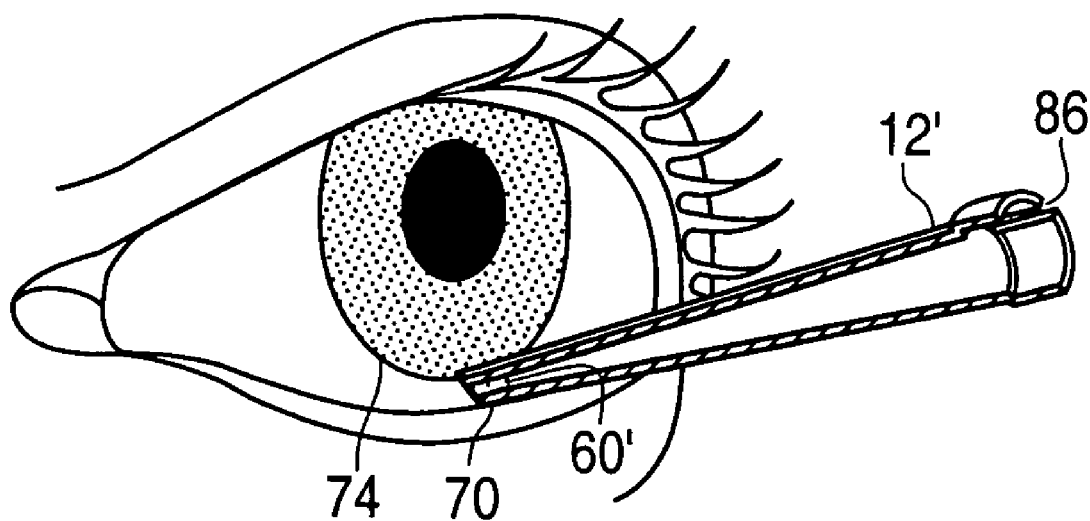

FIGS. 6A–6E illustrate the views of the sample cells 12' in accordance with the present invention. The sample cell 12' is constructed from a plastic material, such as polypropylene, having molecular and surface characteristics which promote the direct collection of samples at the tip of the sample cell as the result of capillary attraction or other attraction phenomenon between the sample 60', and the walls 68 of the tip of the sample cell at the collecting end 70 thereof. The collecting end 70 is inserted directly into contact with the sample to be collected, such as at the corner of the human eye 74. The tip 70 preferably has a cylindrical section 76, but it should be understood that the invention is not limited thereto and a section within the longitudinal passage 78 which tapers outwardly toward the far end 80 to provide a greater area at the far end of the passage. In a typical use of the sample cell for direct collection, a repeatable collected minimum sample volume 60' is achieved which extends beyond the inner termination of the cylindrical section as indicated by line 82 and may extend upwardly for some distance as identified by line 84 which is achieved and maintained by capillary attraction of the collecting end with the sample source such as illustrated in FIG. 6E. In a preferred application, the taper from the interior line 78 up to the far end of the cylindrical section of the sample cell 12' is continuous and the wall of the sample cell is substantially a same thickness along at least a longitudinal portion of the passage which is in thermal contact with the cooling block 42. The sample cell 12' has at least one opening 86 in proximity to the far end for equalizing air pressure in the longitudinal passage 78 during positioning of the sample cell in thermal contact with the cooling block 42 of the heating and cooling assembly 14 as illustrated in FIG. 3. This facilitates retention within the sample cell of a volume of sample 60' which is at a minimum somewhat above the end of the cylindrical section 76. The plastic material preferably used to manufacture the sample cell 12' or other material preferably provides at least partial reflection of the light from a surface of the longitudinal passage 78 to enhance visual contrast between solid and liquid portions in the sample 60' during phase change of the sample.

The practice of the method of the present invention may be as follows for measuring a temperature at which phase change occurs in a sample 60' with an apparatus including a temperature sensing device 44 for sensing a temperature of the sample 60' held in the sample cell 12' to provide direction collection of the sample from a sample source 74 which is collected and retained at a collecting end 70 thereof by capillary attraction between the collecting end and the sample with the sample cell including a longitudinal passage 78 extending from the collecting end to a far end through which light is transmitted to provide an image of the sample retained at the collecting end of the passage with a cross-sectional area of the passage being greater at the far end than at the collecting end, a heating and cooling assembly 14 including the temperature sensing device which holds and thermally contacts the sample cell during determining the temperature at which the phase change occurs by the temperature sensing device while the sample is retained at the collecting end, an illumination system for directing a light beam to the collecting end which may be the LED 16, but is not limited thereto, through the sample, through the longitudinal passage and out of the far end to permit viewing the sample to determine the temperature at which the phase change occurs. The method positions the collecting end of the sample cell in contact with the source of the sample to collect the sample by capillary attractions as illustrated in FIG. 6E; positions the sample cell in thermal contact with the heating and cooling assembly 14; cools the sample within the sample cell to cause a first phase change in the sample by refrigerating the sample with the heating and cooling assembly; raises the temperature within the sample within the sample cell with a controlled temperature gradient provided by the heating and cooling assembly to cause a second phase change in the sample; illuminates the collecting end of the sample cell with light from the illumination system during the raising of the temperature of the sample to direct light through the collecting end, through the sample, along the longitudinal passage and out of the far end to provide an image of the sample; views the image of the sample from the far end to visually detect when a first phase change occurs upon freezing and a second phase change occurs upon melting the sample being completed by the application of the controlled temperature gradient; and determines the temperature sensed by the temperature sensing device when the second phase change caused by the raising of the temperature of the sample has just occurred. The aforementioned process provides a more accurate determination of the osmolality of a sample, such as human tears, and further eliminates the tedious and difficult process of transferring by a syringe a collected sample into the sample cell of the prior art which provided less uniform results than that of the present invention. The utilization of capillary attraction as the mechanism for directly collecting the sample from the sample source in the sample cell which is placed in the heating and cooling assembly of the apparatus of the present invention produces more uniform and accurate results with less human intervention than the prior art.

While the present invention has been described in terms of its preferred embodiments, it should be understood that numerous modifications may be made thereto without departing from the spirit and scope of the present invention. It is intended that all such modifications fall within the scope of the appended claims.

What is claimed is:

1. An apparatus for determining a temperature at which a phase change occurs in a fluid sample comprising:

a sample cell for providing direct collection of the sample from a sample source which is collected and retained at a collecting end thereof by capillary attraction between the collecting end and the sample, the sample cell including a longitudinal passage extending from the collecting end to a far end through which light is transmitted to provide an image of the sample as retained at the collecting end of the passage and with a cross sectional area of the passage being greater at the far end than at the collecting end;

a heating and cooling assembly, including a temperature sensing device, the heating and cooling assembly holding and thermally contacting the sample cell during determining of the temperature by the temperature sensing device at which the phase change occurs while the sample is positioned in the collecting end; and an illumination system for directing a light beam to the collecting end, through the sample, through the longitudinal passage and out of the far end to permit viewing of the sample from the far end to determine the temperature at which the phase change occurs.

2. An apparatus in accordance with claim 1 comprising:

a temperature measuring device associated with the heating and cooling assembly which determines the temperature of the sample held in the sample cell when the sample cell is in thermal contact with the heating and cooling assembly.

3. An apparatus in accordance with claim 1 wherein:
the longitudinal passage at the collecting end comprises a section which collects and retains the sample by the capillary attraction which extends from an opening at the collecting end into the passage and a tapered section tapering outwardly from an interior end of the section within the passage toward the far end to provide the greater area at the far end of the passage whereby the collecting end contains the sample to achieve a repeatable minimum collected sample volume in the collecting end to improve consistency in determining the temperature at which the phase change occurs.

4. An apparatus in accordance with claim 2 wherein:
the longitudinal passage at the collecting end comprises a section which collects and retains the sample by the capillary attraction which extends from an opening at the collecting end into the passage and a tapered section tapering outwardly from an interior end of the section within the passage toward the far end to provide the greater area at the far end of the passage whereby the collecting end contains the sample to achieve a repeatable minimum collected sample volume in the collecting end to improve consistency in determining the temperature at which the phase change occurs.

5. An apparatus in accordance with claim 3 wherein:
the taper is continuous.

6. An apparatus in accordance with claim 4 wherein:
the taper is continuous.

7. An apparatus in accordance with claim 1 wherein:
the sample cell has at least one opening in proximity to the far end for equalizing air pressure in the passage during positioning of the sample cell in thermal contact with the heating and cooling assembly after collection of the sample.

8. An apparatus in accordance with claim 2 wherein:
the sample cell has at least one opening in proximity to the far end for equalizing air pressure in the passage during positioning of the sample cell in thermal contact with the heating and cooling assembly after collection of the sample.

9. An apparatus in accordance with claim 3 wherein:
the sample cell has at least one opening in proximity to the far end for equalizing air pressure in the passage during positioning of the sample cell in thermal contact with the heating and cooling assembly after collection of the sample.

10. An apparatus in accordance with claim 4 wherein:
the sample cell has at least one opening in proximity to the far end for equalizing air pressure in the passage during positioning of the sample cell in thermal contact with the heating and cooling assembly after collection of the sample.

11. An apparatus in accordance with claim 5 wherein:
the sample cell has at least one opening in proximity to the far end for equalizing air pressure in the passage during positioning of the sample cell in thermal contact with the heating and cooling assembly after collection of the sample.

12. An apparatus in accordance with claim 6 wherein:
the sample cell has at least one opening in proximity to the far end for equalizing air pressure in the passage during positioning of the sample cell in thermal contact with the heating and cooling assembly after collection of the sample.

13. An apparatus in accordance with claim 1 comprising:
a camera to provide an image of the sample and a display device for reproducing the image provided by the camera.

14. An apparatus in accordance with claim 2 comprising:
a camera to provide an image of the sample and a display device for reproducing the image provided by the camera.

15. An apparatus in accordance with claim 3 comprising:
a camera to provide an image of the sample and a display device for reproducing the image provided by the camera.

16. An apparatus in accordance with claim 4 comprising:
a camera to provide an image of the sample and a display device for reproducing the image provided by the camera.

17. An apparatus in accordance with claim 5 comprising:
a camera to provide an image of the sample and a display device for reproducing the image provided by the camera.

18. An apparatus in accordance with claim 6 comprising:
a camera to provide an image of the sample and a display device for reproducing the image provide by the camera.

19. An apparatus in accordance with claim 7 comprising:
a camera to provide an image of the sample and a display device for reproducing the image provided by the camera.

20. An apparatus in accordance with claim 19 wherein:
the illumination system comprises a light emitting diode.

21. An apparatus in accordance with claim 1 wherein:
the apparatus is an osmometer for determining a concentration of solutes in a liquid solution of the sample.

22. An apparatus in accordance with claim 21 wherein:
the sample is human tears and the sample cell has an exterior which tapers toward the near end to facilitate collection from an eye of a human.

23. An apparatus in accordance with claim 2 wherein:
the apparatus is an osmometer for determining a concentration of solutes in a liquid solution of the sample.

24. An apparatus in accordance with claim 23 wherein:
the sample is human tears and the sample cell has an exterior which tapers toward the near end to facilitate collection from an eye of a human.

25. An apparatus in accordance with claim 3 wherein:
the apparatus is an osmometer for determining a concentration of solutes in a liquid solution of the sample.

26. An apparatus in accordance with claim 25 wherein:
the sample is human tears and the sample cell has an exterior which tapers toward the near end to facilitate collection from an eye of a human.

27. An apparatus in accordance with claim 1 wherein:
a wall of the sample cell is substantially a same thickness along at least a longitudinal portion of the passage which is in thermal contact with the heating and cooling assembly.

28. An apparatus in accordance with claim 21 wherein:
a wall of the sample cell is substantially a same thickness along at least a longitudinal portion of the passage which is in thermal contact with the heating and cooling assembly and a cylindrical section at the collecting end has a diameter that is approximately twice that of the thickness.

29. An apparatus in accordance with claim 22 wherein:
a wall of the sample cell is substantially a same thickness along at least a longitudinal portion of the passage which is in thermal contact with the heating and cooling assembly.

30. An apparatus in accordance with claim 23 wherein:
a wall of the sample cell is substantially a same thickness along at least a longitudinal portion of the passage which is in thermal contact with the heating and cooling assembly.

31. An apparatus in accordance with claim 24 wherein:
a wall of the sample cell is substantially a same thickness along at least a longitudinal portion of the passage which is in thermal contact with the heating and cooling assembly.

32. An apparatus in accordance with claim 25 wherein:
a wall of the sample cell is substantially a same thickness along at least a longitudinal portion of the passage including the cylindrical section which is in thermal contact with the heating and cooling assembly.

33. An apparatus in accordance with claim 26 wherein:
a wall of the sample cell is substantially a same thickness along at least a longitudinal portion of the passage including the cylindrical section which is in thermal contact with the heating and cooling assembly.

34. An apparatus in accordance with claim 1 wherein:
the sample cell is manufactured from a plastic material providing at least partial reflection of the light beam from a surface of the longitudinal passage to enhance visual contrast between solid and liquid portions in the sample during a phase change of the sample.

35. A method for measuring a temperature at which a phase change occurs in a sample, with an apparatus including a temperature sensing device for sensing a temperature of the sample held in a sample cell to provide direct collection of the sample from a sample source which is collected and retained at a collecting end thereof by capillary attraction between the collecting end and the sample, the sample cell including a longitudinal passage extending from the collecting end to a far end through which light is transmitted to provide an image of the sample retained at the collecting end of the passage with a cross sectional area of the passage being greater at the far end than at the collecting end, a heating and cooling assembly including the temperature sensing device which holds and thermally contacts the sample cell during determining the temperature at which the phase change occurs by the temperature sensing device at which the phase change occurs while the sample is retained at the collecting end, an illumination system for directing a light beam to the collecting end, through the sample, through the longitudinal passage and out of the far end to permit viewing of the sample to determine the temperature at which the phase change occurs comprising the steps:
positioning the collecting end of the sample cell in contact with a source of the sample to collect the sample by capillary attraction;
positioning the sample cell in thermal contact with the heating and cooling assembly;
cooling the sample within the sample cell to cause a first phase change in the sample by refrigerating the sample with the heating and cooling assembly;
raising a temperature of the sample within the sample cell with a controlled temperature gradient provided by the heating and cooling assembly to cause a second phase change in the sample;
illuminating the collecting end of the sample cell with light from the illumination system during the raising the temperature of the sample to direct light through the collecting end, through the sample, along the longitudinal passage and out of the far end to provide an image of the sample;
viewing the image of the sample from the far end to visually detect when a first phase change occurs upon freezing and a second phase change occurs upon melting the sample being completed by the application of the controlled temperature gradient; and
determining the temperature sensed by the temperature sensing device when the second phase change caused by raising the temperature of the sample has occurred.

36. A method in accordance with claim 35 wherein:
the longitudinal passage comprises a section which collects and retains the sample by the capillary attraction which extends from an opening at the collecting end into the passage and a tapered section tapering outwardly from an interior end of the section within the passage toward the far end to provide a greater area at the far end of the passage whereby at least the section at the collecting end contains the sample to achieve a repeatable minimum collected sample volume in the collecting end to improve a consistency in determining the temperature at which the phase change occurs.

37. An apparatus in accordance with claim 35 wherein:
a wall of the sample cell is substantially a same thickness along a portion of the passage which is in thermal contact with the heating and cooling assembly.

38. A method in accordance with claim 37 wherein:
the taper is continuous.

39. A method in accordance with claim 36 wherein:
the sample cell has at least one opening in proximity to the far end for equalizing air pressure in the passage during positioning of the sample cell in thermal contact with the heating and cooling assembly after directly collecting of the sample.

40. A method in accordance with claim 35 comprising:
a camera for providing an image of the sample and a display device for reproducing the image provided by the camera; and wherein
the illumination system provides illumination of the sample held in thermal contact with the heating and cooling assembly, the camera provides an image of the sample held in thermal contact with heating and cooling assembly and the display device reproduces the image of the sample.

41. A method in accordance with claim 35 wherein:
the determined temperature is converted into an osmolarity of the sample.

42. A sample cell for use in an apparatus for determining a temperature at which a phase change occurs in a fluid sample including a heating and cooling assembly including a temperature sensing device, the heating and cooling assembly holding and thermally contacting the sample cell during the determining of the temperature by the temperature sensing device at which the phase change occurs while the sample is positioned in the collecting end, and an illumination system for directing a light beam to the collecting end, through the sample, through the longitudinal passage and out of the far end to permit viewing of the sample from the far end to determine the temperature at which the phase change occurs, wherein the sample cell has a tip which provides direct collection of the sample from a sample source which is collected and retained at a collecting end thereof by capillary attraction between the collecting end and the sample, the sample cell including a longitudinal passage extending from the collecting end to a far end through which light is transmitted to provide an image of the sample as retained at the collecting end of the passage and with a cross sectional area of the passage being greater at the far end than at the collecting end.

* * * * *